US00PP25291P3

(12) United States Plant Patent
Hjeltnes

(10) Patent No.: US PP25,291 P3
(45) Date of Patent: Feb. 17, 2015

(54) PEAR TREE NAMED 'CELINA'

(50) Latin Name: *Pyrus communis*
Varietal Denomination: CELINA

(71) Applicant: Graminor AS, Ridabu (NO)

(72) Inventor: Stein Harald Hjeltnes, Leikanger (NO)

(73) Assignee: Graminor AS, Ridabu (NO)

( * ) Notice: Subject to any disclaimer, the term of this patent is extended or adjusted under 35 U.S.C. 154(b) by 107 days.

(21) Appl. No.: 13/694,445

(22) Filed: Dec. 4, 2012

(65) Prior Publication Data

US 2013/0167273 P1 Jun. 27, 2013

(30) Foreign Application Priority Data

Dec. 26, 2011 (QZ) ..... PBR 20113173

(51) Int. Cl.
*A01H 5/00* (2006.01)

(52) U.S. Cl.
USPC ..... Plt./176

(58) Field of Classification Search
USPC ..... Plt./176
See application file for complete search history.

(56) References Cited

PUBLICATIONS

PLUTO Plant Variety Database search for Celina. Apr. 2014. p 1.*

* cited by examiner

*Primary Examiner* — Annette Para
(74) *Attorney, Agent, or Firm* — Foley & Lardner LLP

(57) ABSTRACT

A new and distinct *Pyrus communis* pear tree variety named 'CELINA' particularly characterized by its green-yellow fruit with a red blush, pyriform/straight to convex fruit shape, fine fruit texture, medium fruit size, high yield, early fruit maturation, and resistance to scab.

4 Drawing Sheets

Latin name of the genus and species of the plant claimed: *Pyrus communis.*

Variety denomination: 'CELINA'.

BACKGROUND OF THE INVENTION

The present invention relates to a new and distinct variety of pear tree, botanically known as *Pyrus communis* of the Rosaceae family, and hereinafter referred to by the variety denomination 'CELINA'.

The new *Pyrus* variety is a product of a controlled breeding program conducted by the inventor, Stein Harald Hjeltnes, in Balsgård, Kristianstad, Sweden. The objective of the breeding program was to develop a new *Pyrus* variety with early maturation, high fruit quality, good shelf life, attractive fruits, high and stable production.

The new *Pyrus* variety originated from a cross made by the inventor in 1985 in Balsgård, Kristianstad, Sweden. The female or seed parent is the *Pyrus communis* variety designated 'Colorée de Juillet', unpatented. The male or pollen parent is the *Pyrus communis* variety designated 'Williams', unpatented. The new *Pyrus* variety was discovered and selected by the inventors within the progeny of the stated cross in a controlled environment in 1997 in Njøs, Leikanger, Norway.

BRIEF DESCRIPTION OF THE INVENTION

The following traits have been repeatedly observed and are determined to be unique characteristics of 'CELINA' which in combination distinguish this pear tree as a new and distinct variety:

1. Fruit color: dark red blush with small red dots at lenticels, green-yellow background
2. Fruit shape: pyriform, straight to convex
3. Fruit flesh texture: fine
4. Fruit size: medium
5. Fruit number: high, productive
5. Time of maturation: early
6. Leaf color: dark green
7. Leaf shape: medium long and wide
8. Leaf texture: leathery
9. Leaf size: medium-large
10. Flower number: 8-10 flowers per clusters, flowers abundantly
11. Flower color: white with pinkish anthers
12. Flowering time: mid-season
13. Tree growth habit: very vigorous, spreading
14. Disease resistance: resistant to scab In comparison to the parental varieties, 'COLORÉE DE JUILLET' and 'WILLIAMS', 'CELINA' differs primarily in the traits listed in Table 1.

TABLE 1

Comparison with Parent Varieties

| Trait | New Variety 'CELINA' | Female Parent 'COLORÉE DE JUILLET' (unpatented) | Male Parent 'WILLIAMS' (unpatented) |
|---|---|---|---|
| Over color | dark red, speckled, intense | brown to dark red, dotted and striped | Faint blush |
| Fruit shape | Pyriform, straight to convex | Ovate, convex | Oblong-obtuse-pyriform |
| Fruit texture | Fine | Fine | Fine |

TABLE 1-continued

| Comparison with Parent Varieties | | | |
|---|---|---|---|
| Trait | New Variety 'CELINA' | Female Parent 'COLORÈE DE JUILLET' (unpatented) | Male Parent 'WILLIAMS' (unpatented) |
| Fruit size | 150-180 grams | 100-120 grams | 100-150 grams |
| Time of maturation | Early | Extremely early | Early |

Of the many commercial varieties known to the present inventor(s), the most similar in comparison to the new *Pyrus* variety 'CELINA' is the *Pyrus* variety 'Forelle', (unpatented), in the following characteristics described in Table 2:

TABLE 2

| Comparison with Similar Variety | | |
|---|---|---|
| Characteristic | New Variety 'CELINA' | Comparison Variety 'FORELLE' (unpatented) |
| Over colour | intense dark red, speckled | Reddish with trout-like speckles |
| Fruit shape | Pyriform | Oblong-obovate-pyriform |
| Fruit texture | Fine | Fine |
| Fruit size | 150-180 grams | 150-180 grams |
| Time of maturation | Early | Medium - late |

BRIEF DESCRIPTION OF THE DRAWINGS

The accompanying photographs illustrate the overall appearance of the new *Pyrus* variety 'CELINA' showing the colors as true as is reasonably possible with colored reproductions of this type. Colors in the photographs may differ slightly from the color values cited in the detailed botanical description, which accurately describe the color of 'CELINA'.

DETAILED BOTANICAL DESCRIPTION

Figure 1:
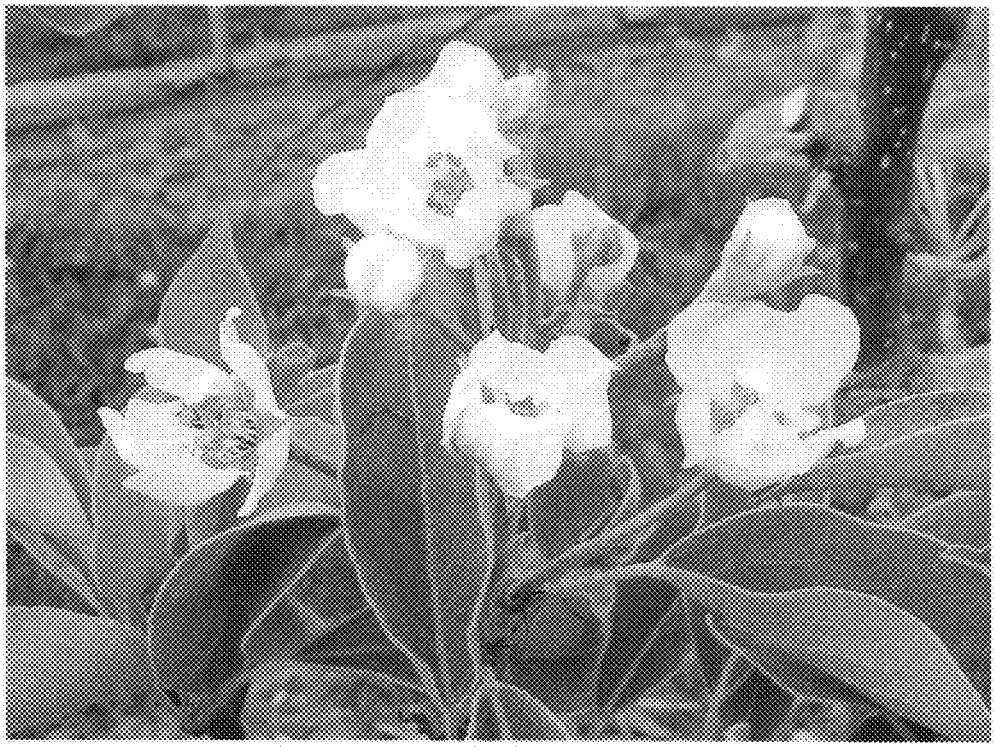
FIG. 1—shows a flower cluster of 'Celina'
Figure 2:
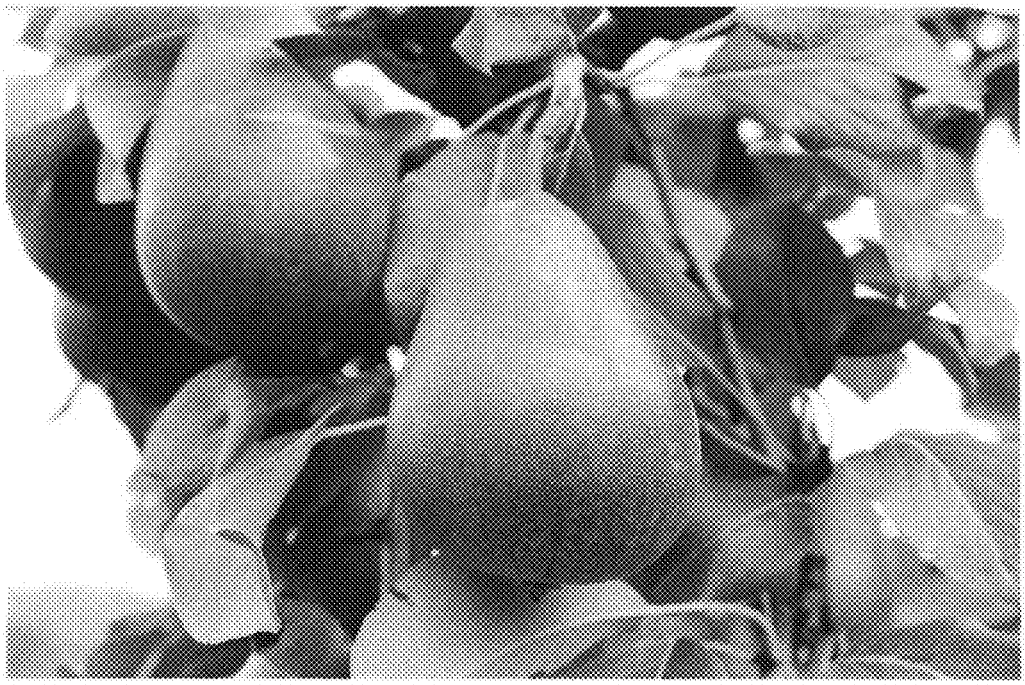
FIG. 2—shows typical fruits of 'Celina'
Figure 3:
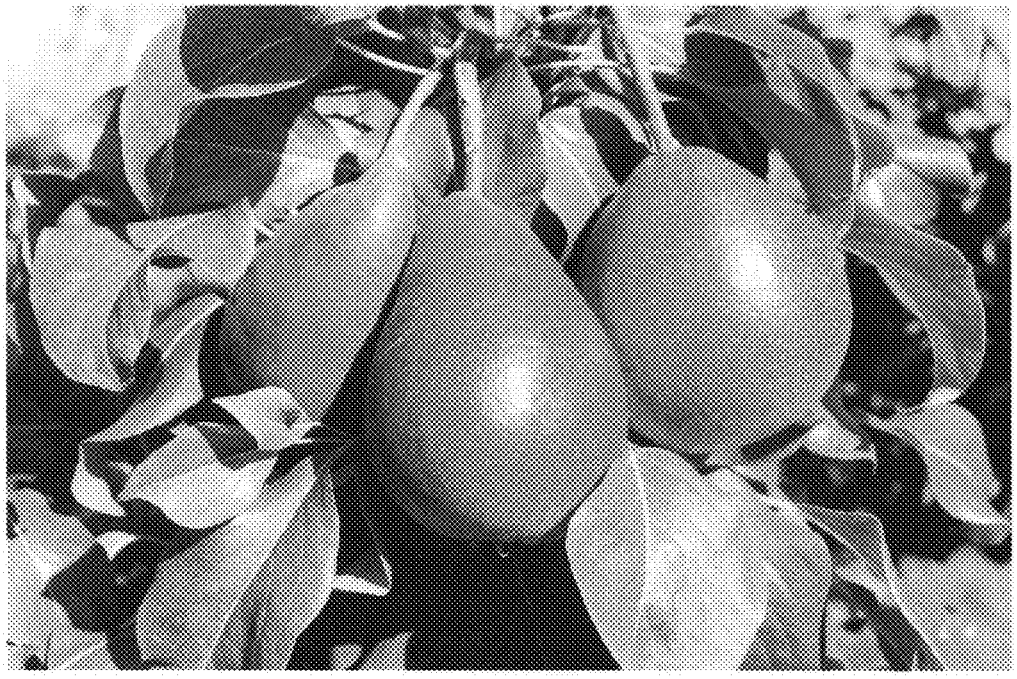
FIG. 3—shows well exposed 'Celina' fruits on a sunny day.
Figure 4:
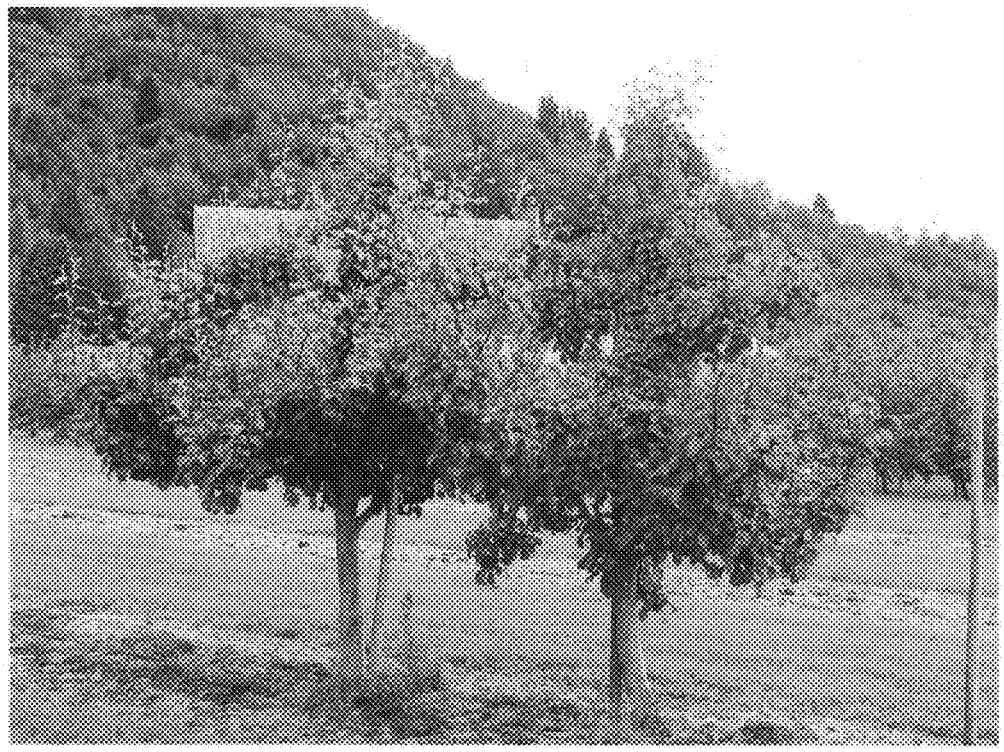
FIG. 4—shows 14 year old trees of 'Celina' with fruitlets on Aug. 1, 2012 (about 7 weeks prior to harvest).

The new *Pyrus* variety 'CELINA' has not been observed under all possible environmental conditions. The phenotype of the new variety may vary with variations in environment such as temperature, light intensity, and day length without any change in the genotype of the pear tree.

The aforementioned photographs, together with the following observations, measurements and values describe trees of 'CELINA' as grown in Njøs, Leikanger, Norway, under conditions which closely approximate those generally used in commercial practice. Field trials were done with black plastic mulching and trickle irrigation, spaced 4×2 meter. Mean temperatures in May-September were approximately 13° C., with (rarely) maximum temperatures above 25° C. Daily mean temperatures were 15-20° C., 30-years normal average was 15° C. Winters were mild winters, rarely under −10° C. Mean temperature in the coldest month was −1° C. Fertilization was 50 kg N, 20 kg P and 70 kg K per ha).

Unless otherwise stated, the detailed botanical description includes observations, measurements and values based on 6 to 14 year old 'CELINA' trees grown in Njøs—Leikanger, Norway, from 1998 to 2012. Quantified measurements are expressed as an average of measurements taken from a number of trees of 'CELINA'. The measurements of any individual tree, or any group of trees, of the new variety may vary from the stated average.

Color references are made to The Royal Horticultural Society Colour Chart (R.H.S.), fifth edition, 2007, except where general colors of ordinary significance are used. Color values were taken under daylight conditions at approximately 2 pm in Njøs—Leikanger, Norway.

All of the trees of 'CELINA', insofar as they have been observed, have been identical in all the characteristics described below.

Classification:

*Botanical.*—*Pyrus communis.*

*Commercial.*—*Pyrus* cv. Celina.

*Variety name.*—CELINA.

Parentage:

*Female or seed parent.*—*Pyrus* variety designated 'COLORÉE DE JUILLET' (unpatented).

*Male or pollen parent.*—*Pyrus* variety designated 'WILLIAMS' (unpatented).

Propagation: Grafted on rootstock: *Pyrus communis* 'Kirschensaller Mostbirne' seedling.

Growing conditions:

*Light intensities.*—Full sunlight.

*Temperature.*—During day, grown in range of 10° C. to 25° C., and during evening, grow in range of 5° C. to 15° C.

*Fertilization.*—A balanced fertilizer with level of 50 kg N, 20 kg P and 70 kg K per ha.

*Growth regulators.*—No growth regulators applied.

*Pruning or trimming requirements.*—No specific requirements.

Tree:

*Age.*—Observed trees were 14 years old.

*Vigor.*—High vigor; early onset of production; high productivity and abundant early flowering.

*Form.*—Spreading and pyramidal.

*Habit.*—A large sized tree with one trunk and usually one leader; main branches spreading; crown symmetrical and pyramidal in shape. Tree is trained to a defined system, that has been modified the last 4 years.

*Branching habit.*—Main branches angle is 60° to 90° with respect to trunk if allowed to grow naturally. Trees have not been grown naturally.

*Density.*—Medium density.

*Size at maturity.*—Depends on space available. Truncated to: Height: About 3.5 m. Spread: About 2 m.

*Trunk.*—Height (up to leaders): About 0.8 m. Diameter: About 0.11 m. Texture: At first, smooth with numerous lenticels, and the trunk stays smooth. Bark color: Primarily RHS 195C, with RHS 162C underbark. Trunk lenticels: Length: About 15 mm. Width: About 2 mm. Color: RHS 199B. Density: 2/cm$^2$.

*Branches.*—Number per tree: About 8. Length: Varies due to the shape of tree; maximum of 100 cm to 140 cm; minimum of 40 cm to 60 cm. Diameter: About 30 mm to 50 mm. Surface texture: smooth. Color: Mature (after about 4 years): RHS 197B. New Growth: RHS 183C. Internode length: About 3.2 cm to 3.6 cm. Internode diameter: About 6 mm to 7 mm. Branch lenticels: Length: About 3 mm. Width: About 1 mm. Color: RHS 197B. Density: 2/cm$^2$.

*Spur*.—Present: Yes. Distance between each spur: about 20 mm to 40 mm (on the four year old branches). Diameter of each spur: About 8. Number of fruit per spur: About 1 to 3.

*Leaves*.—Arrangement: Alternate. Lamina: Size: Length: About 100 mm (from 95 to 105 at fully expanded leaf). Width: About 65 mm (from 62 to 68 at fully expanded leaf). Length/width ratio: 1.5. Overall shape: curved, not regular. Base shape: Acute to right angled. Apex shape: acute. Margin: crenate, undulated. Texture: Upper surface: glabrous. Under surface: glabrous. Pubescence: Upper surface: some silver-colored at the main vein, else glabrous. Under surface: some silver-colored at the main vein, some at secondary veins. Color (mature leaves): Upper surface: RHS 135A. Under surface: RHS 136B. Color (immature leaves): Upper surface: RHS 144B. Under surface: RHS 144A.

*Venation*.—Type: venation from central vein to the leaf edge. Color: RHS 145B.

*Petiole*.—Length: About 50 mm. Diameter: About 1 mm. Color: RHS 145B.

*Stipule*.—Arrangement: adnate. Length (distance of stipules from basal attachment of petiole):About 4 mm to 5 mm. Width: About 0.5 mm to 1 mm.

INFLORESCENCE:

*Buds*.—Terminal Buds: Number per spur: About 2. Shape: Triangular. Length: About 8 mm. Width: About 5 mm. Color: Apex, RHS 183A, and base, RHS 178A. Texture: Smooth. Pubescence: Pubescent, villous. Color: RHS 156B. Scales: Number: About 10. Overall shape: Mucronate. Apex shape: Mucronate. Base shape: Truncate. Color: Upper: RHS 183A. Lower: RHS 160B.

*Lateral buds*.—Number per spur: About 3. Shape: Turbinate. Length: About 7 mm. Width: About 4 mm. Color: Apex, RHS 183A, and base, RHS 178A. Texture: Smooth. Pubescence: Pubescent, villous. Color: RHS 156 B. Scales: Number: About 10. Overall shape: Mucronate. Apex shape: Mucronate. Base shape: Truncate. Color: Upper: RHS 183A. Lower: RHS 160B.

*Blooming time*.—Full bloom on about May 20$^{th}$.

*Blooming period*.—About 10 to 14 days.

*Fragrance*.—Slight maltose fragrance.

*Type*.—Corymb.

*Number of flowers per inflorescence*.—About 8 to 10.

*Inflorescence size*.—Diameter: About 9 cm. Depth: About 8 cm.

*Petals*.—Number per flower: Five. Size: Length: About 18 mm. Width: About 15 mm. Length/width ratio: 1.2. Overall shape: Round. Apex curves slightly about ⅓ over the flower center. Apex shape: Even, not flattened or elongated. Base shape: funnel-shaped, about 4 mm long. Texture (upper surface): Slightly heightened longitudinal profiles. Texture (lower surface): Slightly heightened longitudinal profiles. Margin: Even. Color (upper surface): Apex, RHS 155A, and base, RHS 155A. Color (lower surface): Apex, RHS 155A and base, RHS 155A.

*Sepals*.—Number per flower: Five. Size: Length: About 5 mm. Width: About 3 mm. Length/width ratio: 1.7. Overall shape: triangular. Apex shape: pointed, curves inwards. Base shape: inflates towards base. Texture (upper surface): tomentose. Texture (lower surface): tomentose. Margin: Even. Color (upper surface): Apex, RHS 138B and base, RHS 138B. Color (lower surface): Apex, RHS 138A and base, RHS 138A.

*Pedicel*.—Length: 20 to 22 mm. Diameter: 1 to 2 mm. Texture: Tomentose. Color: RHS 155A.

Reproductive organs:

*Androecium*.—Stamen: Number: 20. Length: About 7 mm. Color: RHS 155A. Anthers: Color: RHS 74B. Shape: Curved, deep furrow. Length: About 1.5 mm. Filaments: Length: About 5 mm. Color: RHS 155A. Pollen: Amount: Abundant. Color: RHS 11D. Pollination Requirements: Requires pollinators, e.g. 'Conférence'.

*Gynoecium*.—Pistils: Quantity: 5. Length: About 8 mm. Stigmas: Shape: Ovate, tomentose. Length: About 0.9 mm. Width: About 0.7 mm. Color: RHS 127B. Ovary: Shape: Ovate. Position: Under stamen. Length: About 6 mm. Width: About 5 mm. Color: RHS 126B Fruit:

*Keeping quality*.—The fruit keeps well on the tree and doesn't easily drop. It can be stored in cold temperature conditions for up to 3 months without losing firmness and juiciness. It has a shelf life of at least 1 week without losing firmness and juiciness. Firmness is approximately at 1.8 kg/cm$^2$ after 12 days at 20° C. following 2 months of storage at −0.5° C. More than 3 months of storage in standard atmosphere will give faster drop in firmness. 1.4 kg/cm will be experienced in less than one week. This behavior is typical when harvesting at about 6 kg/cm$^2$.

*Maturity when described*.—Ripe for eating.

*Maturity period after full bloom*.—About 118 days after full bloom on May 20$^{th}$ in Norway.

*Type*.—Pome.

*General shape*.—Turbinate.

*Average weight*.—About 150 g.

*Fruit size*.—Average height: About 75 mm. Average diameter (at widest point): About 65 mm. Height/thickness ratio: 1.15.

*Stem*.—Length: About 25 mm. Diameter: About 3.5 mm. Color: RHS B144.

*Basin*.—Depth: About 1 mm. Width: About 15 mm.

*Calyx*.—Depth: About 1 mm. Width: About 25 mm. Crowning at calyx end: semi-closed. Calyx tube: Funnel shaped.

*Skin*.—Thickness: Medium to thin. Texture: fine. Firmness (at picking time): 5 to 6 kg/cm$^2$. Color: RHS 144C. Lenticels: Length: About 1 mm. Width: About 1 mm. Color: RHS 144A. Density: 30 n°/cm$^2$.

*Flesh*.—Color: RHS 1D. Texture: tender, fine, juicy. Aroma: slight. Sugar content (at picking time): 11 to 13 Brix. Acidity/Starch (at picking time): 1.3 to 2.0 g/lt. Core: Symmetry of core: symmetric. Distinctness of core lines: green, medium visible. Locules: Number (per fruit): 5. Length: About 16 mm. Width: About 3 mm. Form: closed.

Seeds:

*Number per fruit*.—About 2 to 10.

*Number per locule*.—About 2.

*Shape*.—Oval.

*Length*.—About 10 mm.

*Width.*—About 4 mm.

*Color.*—RHS 202A.

Use: Fresh market.

Disease/pest resistance: Resistance to scab.

Disease/pest susceptibility: None observed.

Winter hardiness: Tolerant to temperatures down to −20° C. without observed damage to wood and buds of dormant pear trees (observed in experimental field in Eastern Norway); but open flowers and young fruitlets are killed by exposure to −3° C., depending on the length of exposure.

Drought/heat tolerance: No information available.

I claim:

1. A new and distinct *Pyrus communis* pear tree variety named 'CELINA', as illustrated and described herein.

* * * * *